United States Patent [19]

van der Jagt

[11] Patent Number: Plant 5,973

[45] Date of Patent: May 5, 1987

[54] CHRYSANTHEMUM

[75] Inventor: Martinus van der Jagt, Ter Aar, Netherlands

[73] Assignee: Chrysanthemum Breeders Association N.V., Willemstad, Netherlands Antilles

[21] Appl. No.: 599,557

[22] Filed: Apr. 12, 1984

[51] Int. Cl.[4] ..... A01H 5/00

[52] U.S. Cl. ..... Plt./76

[58] Field of Search ..... Plt./76, 80

*Primary Examiner*—Robert E. Bagwill

*Attorney, Agent, or Firm*—Parkhurst & Oliff

[57] ABSTRACT

A new and distinct variety of Chrysanthemum plant named 'Remember', bearing medium sized pink blooms with a yellow-green center and a performance of fourteen days.

3 Drawing Figures

BACKGROUND OF THE NEW PLANT

The new plant of the present invention relates to the Chrysanthemum genus.

ORIGIN AND HISTORY OF THE PLANT

The new plant according to the present invention comprises a new and distinct cultivar of Chrysanthemum plant which is a cross of parents known as "Dramatic" and "Refour". The new cultivar was discovered by Martinus van der Jagt in May, 1982 at Paradijsweg 88, Ter Aar, Holland. The new cultivar has been asexually reproduced by cuttings at the same location, and has been found to retain its distinctive characteristics through successive propagations.

SUMMARY OF THE NEW PLANT

The present invention is a new and distinct variety of Chrysanthemum of a medium sized bloom and pink color.

BRIEF DESCRIPTION OF THE DRAWINGS

The present new and distinct chrysanthemum cultivar is shown in the accompanying drawings, the color being as nearly true as possible with color photographs of this type.

Sheet 1 shows the fully mature bloom of the new cultivar;

Sheet 2 shows various stages of bloom of the new cultivar; and

Sheet 3 shows the foliage and petiole of the new cultivar.

DESCRIPTION OF THE NEW PLANT

This new variety of Chrysanthemum is of the botanical classification *Chrysanthemum morifolium,* named 'Remember'. When grown in the vicinity of Ter Aar, Holland, it has a response time of approximately eight and one-half weeks. This new variety produces medium sized pink blooms with a yellow-green center having a performance of fourteen days. This new variety of Chrysanthemum has been found to retain its distinctive characteristics throughout successive propagations and may be planted under conventional greenhouse conditions in Holland.

The following is a description of the plant and characteristics that distinguish it over related known varieties and its antecedents:

Botanical classification: *Chrysanthemum morifolium.*

Bud:

*Size.*—Small, cross section 0.8 cm., height 1.0 cm.

*Form.*—Oval.

*Outside color.*—Red-purple RHS 74 C.

Bloom:

*Size.*—Medium.

*Fully expanded.*—7½ cm.

*Borne.*—Single.

*Stems.*—Strong.

*Forms.*—Anemone type.

*Permanence.*—14 days (at 18°-20° C.).

Color:

*Center of flower (Disk Floret).*—The spot in the middle of the cushion. Yellow-green RHS 147 C.

*Base of petals.*—Red-purple RHS 74 C.

*Inside of petals.*—Red-purple RHS 74 C.

*Reverse of petals.*—Red-purple RHS 69 C.

*Outer petals.*—Purple RHS 75 A.

*Tonality from a distance.*—Anemone type with pastel color. When not overbloomed, the "cushion" has a small greyed-green spot in the middle giving a fresh look.

*Fully mature (Discoloration).*—Red-purple RHS 69 C.

Petals:

*Texture (upper and underside).*—Smooth.

*Number.*—33-38 (*not* including the "cushion").

*Cross-section.*—Convex, no keels.

*Arrangement.*—Imbricated.

*Persistence.*—Normal. Petals reflex when overbloomed (after 14 days).

*Fragrance.*—Chrysanthemum.

Reproductive organs:

*Stamen.*—Some in the petals of the cushion (center).

*Pollen.*—Some appear when blooming.

*Styles.*—Columnar, Green-yellow.

*Length.*—Short, 3 mm.

*Stigmas.*—Green-yellow, 0.6 mm wide.

*Ovaries.*—Enclosed in calyx.

Plant:

*Form.*—Single stem spray meant for erect culture.

*Growth.*—Medium.

*Height.*—95 cm.

*Peduncle.*—Near the Top — 12 cm. Near the Middle — 16 cm. Near the Bottom — 24 cm.

*Internodes.*—3–4 cm.

*Flowering response.*—Eight and one-half weeks.

Foliage:

*Color.*—Green.

*Size.*—Length 9 cm., width 7 cm.

*Quantity.*—25–30.

*Shape.*—Oval, some undulated.

*Texture.*—Upperside — Rough. Underside — Smooth.

*Ribs and veins.*—Not well developed. Upperside: Both easily visible. Underside: Ribs not easy to see, veins appear normal.

*Edge.*—Undulated.

*Leaf underside.*—Smooth, a thick hirsuteness.

In the description above, color references are made to the "R.H.S. Colour Chart" issued by The Royal Horticultural Society in association with the Flower Council of Holland, February 1986.

What is claimed is:

1. A new and distinct variety of Chrysanthemum named 'Remember', as described and illustrated in the foregoing specification and accompanying drawings.

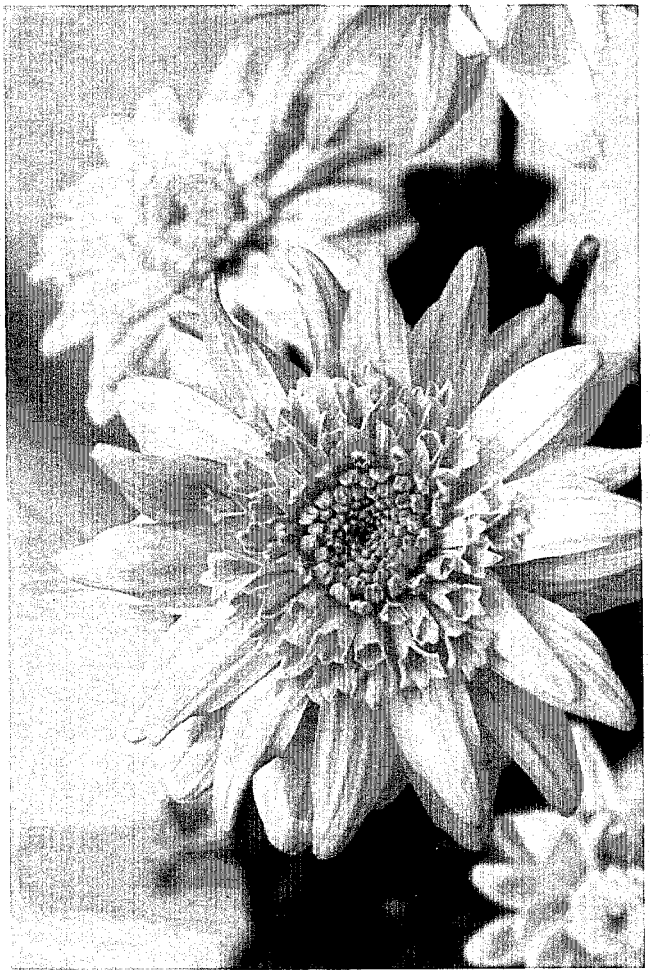

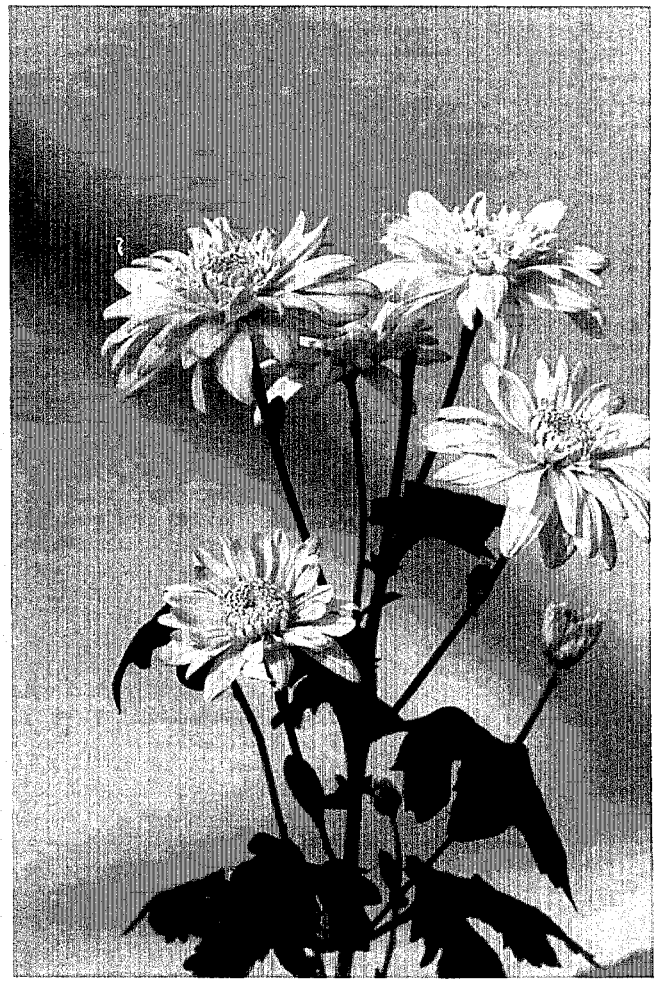

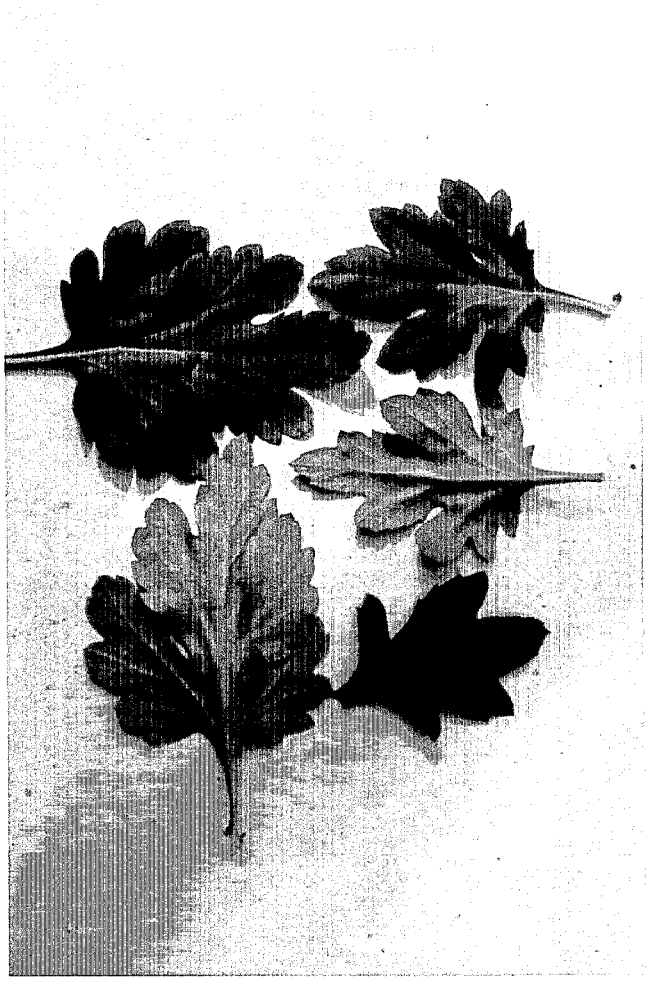

* * * * *